US011744538B2

(12) United States Patent
Li et al.

(10) Patent No.: US 11,744,538 B2
(45) Date of Patent: Sep. 5, 2023

(54) SYSTEM AND METHOD FOR QUANTIFYING LUMINAL STENOSIS USING MULTI-ENERGY COMPUTED TOMOGRAPHY IMAGING

(71) Applicant: Mayo Foundation for Medical Education and Research, Rochester, MN (US)

(72) Inventors: Zhoubo Li, Libertyville, IL (US); Cynthia H. McCollough, Byron, MN (US); Lifeng Yu, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 494 days.

(21) Appl. No.: 16/463,331

(22) PCT Filed: Nov. 21, 2017

(86) PCT No.: PCT/US2017/062704
§ 371 (c)(1),
(2) Date: May 22, 2019

(87) PCT Pub. No.: WO2018/098118
PCT Pub. Date: May 31, 2018

(65) Prior Publication Data
US 2019/0374183 A1   Dec. 12, 2019

Related U.S. Application Data

(60) Provisional application No. 62/425,923, filed on Nov. 23, 2016.

(51) Int. Cl.
*A61B 6/00* (2006.01)
*A61B 6/03* (2006.01)

(52) U.S. Cl.
CPC .............. *A61B 6/504* (2013.01); *A61B 6/032* (2013.01); *A61B 6/469* (2013.01); *A61B 6/482* (2013.01);
(Continued)

(58) Field of Classification Search
CPC .......... G16H 50/30; A61B 6/03; A61B 6/032; A61B 6/469; A61B 6/482; A61B 6/484; A61B 6/504; A61B 6/5217; A61B 6/583
See application file for complete search history.

(56) References Cited

U.S. PATENT DOCUMENTS 7,852,986 B2    12/2010  Loef
2004/0101086 A1*  5/2004  Sabol ............... A61B 6/482
                                                378/4
(Continued)

FOREIGN PATENT DOCUMENTS

JP      2630911 B2 *  7/1997  ............. A61B 6/03
WO     201592588       6/2015

OTHER PUBLICATIONS

Ota, H. et al. "Quantitative Vascular Measurements in Arterial Occlusive Disease", RadioGraphics, 25:1141-1158. (2005) (Year: 2005).*

(Continued)

*Primary Examiner* — Boniface Ngathi N
*Assistant Examiner* — Milton Truong
(74) *Attorney, Agent, or Firm* — QUARLES & BRADY LLP

(57) ABSTRACT

A system and method for determining stenosis severity in a subject's vasculature using multi-energy computer tomography (MECT) imaging is provided. In some aspects, the method includes acquiring MECT data using a CT system, performing a material decomposition process on acquired MECT data to generate one or more material density maps,
(Continued)

and selecting, using the one or more material density maps, one or more regions of interest (ROIs) encompassing at least one vessel cross-section. The method also includes measuring an iodine content in the one or more ROIs, and determining a stenosis severity based on the measured iodine content. The method further includes generating a report indicating the stenosis severity associated with the subject's vasculature.

12 Claims, 11 Drawing Sheets

(52) U.S. Cl.
CPC ............ *A61B 6/484* (2013.01); *A61B 6/5217* (2013.01); *A61B 6/583* (2013.01)

(56) References Cited

U.S. PATENT DOCUMENTS

| | | | |
|---|---|---|---|
| 2004/0101088 A1 | 5/2004 | Sabol | |
| 2004/0136491 A1* | 7/2004 | Iatrou | A61B 6/4035 378/4 |
| 2010/0135453 A1 | 6/2010 | Mendonca | |
| 2013/0066197 A1* | 3/2013 | Pruvot | A61B 6/504 600/427 |
| 2015/0141814 A1 | 5/2015 | Lee et al. | |
| 2016/0123904 A1 | 5/2016 | Masood et al. | |
| 2016/0206265 A1 | 7/2016 | Schmitt et al. | |

OTHER PUBLICATIONS

Kruger, R.A. "Estimation of the diameter of and iodine concentration within blood vessels using digital radiography devices", Med. Phys. 8(5), 652-658. (1981) (Year: 1981).*

Jinzaki, Masahiro, et al. "Computed Tomography Multispectral Imaging." Multi-Detector CT Imaging. CRC Press, 2013. 585-594. (Year: 2013).*

Biermann C, et al. Evaluation of Computer-Assisted Quantification of Carotid Artery Stenosis. Journal of Digital Imaging. 2012;25(2):250-257.

Bleeker L, et al. Semi-automatic quantitative measurements of intracranial internal carotid artery stenosis and calcification using CT angiography. Neuroradiology. 2012;54(9):919-27.

Borst J, et al. Diagnostic Accuracy of 4 Commercially Available Semiautomatic Packages for Carotid Artery Stenosis Measurement on CTA. American Journal of Neuroradiology. 2015;36(10):1978-87.

Gutjahr R, et al. Human Imaging With Photon Counting-Based Computed Tomography at Clinical Dose Levels: Contrast-to-Noise Ratio and Cadaver Studies. Investigative radiology. 2016.

Hameeteman K, et al. Evaluation framework for carotid bifurcation lumen segmentation and stenosis grading. Medical Image Analysis. 2011;15(4):477-88.

International Searching Authority, International Search Report and Written Opinion for application PCT/US2017/062704, dated Feb. 13, 2018, 8 pages.

Kappler S, et al. First results from a hybrid prototype CT scanner for exploring benefits of quantum-counting in clinical CT. SPIE Medical Imaging: International Society for Optics and Photonics; 2012:83130X-X-11.

Katano H, et al. Analysis of calcium in carotid plaques with agatston scores for appropriate selection of surgical Intervention. Stroke. 2007;38(11):3040-4.

Li, Z, et al. "An effective noise reduction method for multi-energy CT images that exploit spatio-spectral features." Medical physics 44.5 (2017): 1610-1623.

Li, Z, et al. "Image-based material decomposition with a general volume constraint for photon-counting CT." Medical Imaging 2015: Physics of Medical Imaging. vol. 9412. International Society for Optics and Photonics, 2015.

Manniesing R, et al. Robust CTA lumen segmentation of the atherosclerotic carotid artery bifurcation in a large patient population. Medical Image Analysis. 2010;14(6):759-69.

Marquering HA, et al. Performance of Semiautomatic Assessment of Carotid Artery Stenosis on CT Angiography: Clarification of Differences with Manual Assessment. American Journal of Neuroradiology. 2012;33(4):747-54.

McCollough CH, et al. Dual- and Multi-Energy CT: Principles, Technical Approaches, and Clinical Applications. Radiology. 2015;276(3):637-53.

Miralles M, et al. Quantification and characterization of carotid calcium with multi-detector CT-angiography. European journal of vascular and endovascular surgery: the official journal of the European Society for Vascular Surgery. 2006;32(5):561-7.

Porsche C, et al. Evaluation of cross-sectional luminal morphology in carotid atherosclerotic disease by use of spiral CT angiography. Stroke. 2001;32(11):2511-5.

Scherl H, et al. Semi-automatic level-set based segmentation and stenosis quantification of the internal carotid artery in 3D CTA data sets. Medical Image Analysis. 2007;11(1):21-34.

Yu Z, et al. Evaluation of conventional imaging performance in a research whole-body CT system with a photon-counting detector array. Physics in Medicine and Biology. 2016,61(4):1572-95.

Yu Z, et al. Initial results from a prototype whole-body photon-counting computed tomography system. Proceedings of SPIE—the International Society for Optical Engineering, 2015. 4470574.

Zhang Z, et al. Carotid stenosis degree in CT angiography: assessment based on luminal area versus luminal diameter measurements. European radiology. 2005;15(11):2359-65.

Zhu CC, et al. Carotid stenosis assessment with multi-detector CT angiography: comparison between manual and automatic segmentation methods. International Journal of Cardiovascular Imaging. 2013;29(4):899-905.

European Patent Office. Extended European Search Report for application 17874217.7. dated Jul. 17, 2020.

* cited by examiner

SYSTEM AND METHOD FOR QUANTIFYING LUMINAL STENOSIS USING MULTI-ENERGY COMPUTED TOMOGRAPHY IMAGING

CROSS-REFERENCE TO RELATED APPLICATION

This application is based, on claims priority to, and incorporates herein by reference U.S. Application Ser. No. 62/425,923, filed Nov. 23, 2016.

GOVERNMENT RIGHTS

This application is a 371 U.S. National Phase Entry of PCT/US17/062704, filed Nov. 21, 2017, which is based, on claims priority to, and incorporates herein by reference U.S. Application Ser. No. 62/425,923, filed Nov. 23, 2016.

BACKGROUND

The present disclosure relates generally to systems and methods for analyzing computed tomography (CT) imaging and, in particular, to systems and methods for quantifying luminal stenosis using multi-energy CT imaging.

Atherosclerosis is a disease characterized by a thickening of blood vessel walls and the formation of plaque containing calcium, fat, cholesterol, and other substances found in the blood. Causing limited blood flow due to narrowed blood vessels, or stenosis, atherosclerosis is one of primary causes of cardiovascular diseases leading to mortality. For instance, in 2014, 1 out of 6 people in the United Sates died of coronary artery disease, and 1 out of 19 died of stroke. Therefore, the degree of stenosis is an important parameter that is considered when identifying different therapeutic options, which can vary in cost, complications and length of hospital stay. With direct and indirect costs of care being up to more than 300 billion annually atherosclerosis represents a significant burden on private and public health.

Presently, catheter angiography is considered the gold standard method for directly identifying the degree of stenosis in a patient. However, catheter angiography is a costly technique that is invasive and involves high risk. By contrast, non-invasive imaging techniques can provide important alternatives to catheter angiography. For instance, ultrasound imaging is safe and inexpensive. However, the quality of image information obtained using ultrasound is highly dependent on the equipment and the experience of the technologists. Also, performance is limited due to the shallow penetration depth of ultrasound signals. On the other hand, magnetic resonance (MR) angiography can image throughout the body of a patient, but has been shown to overestimate the degree of stenosis. In addition, MR angiography cannot be applied to patients with metal implants.

Computed tomography (CT) angiography is a fast and reliable technique for determining the degree of stenosis. It can be highly sensitive and specific to detecting high-grade stenosis, and generates reproducible image information when used by different operators. However, CT systems measure the attenuation of x-rays, which is a function of the mass attenuation coefficients and densities of materials of the imaged subject. As a result, high density calcification in atheromatous plaque can produce similar pixel intensities on CT images as iodinated arterial lumens. This makes identification of lumen boundaries, and quantification of degree of stenosis, difficult. In addition, significant blooming artifacts may occur in CT images in the presence of heavy calcification. These can further obscure the visibility of lumens, and cause inaccurate estimation of luminal stenosis that may lead to false positives.

Presently, stenosis is quantified on CT images by performing manual or semi-automated segmentation. However, manual segmentation requires careful selection of window and level settings, which is a time consuming process that suffers from inter and intra rater variability. This is because proper window and level settings can depend on calcification density, size, contrast and other factors. On the other hand, semi-automated segmentation algorithms generally have lower sensitivity than manual measurements and the accuracy degrade with calcified plaques.

Hence, in light of the above, there continues to be a need for improved techniques to accurately quantify stenosis severity for the diagnosis and treatment of patients suffering from atherosclerosis.

SUMMARY

The present disclosure overcomes the drawbacks of previous techniques by providing a system and method for determining stenosis severity in a subject's vasculature using multi-energy computer tomography (MECT) imaging. In particular, a novel approach is introduced herein whereby a degree of luminal stenosis may be obtained by generating and processing material density maps, such as iodine, water and calcium density maps. As will be described, by separating image content according to material composition, the present approach can yield highly accurate and reproducible results, which are rather insensitive to different image acquisition parameters or conditions.

In accordance with one aspect of the disclosure, a system for determining stenosis severity in a subject's vasculature using multi-energy computer tomography (MECT) imaging is provided. The system includes an input configured to receive multi-energy computed tomography (MECT) data acquired using a CT system; and a processor programmed to perform a material decomposition process on received multi-energy CT data to generate one or more material density maps, select, using the one or more material density maps, one or more regions of interest (ROIs) encompassing at least one vessel cross-section, and measure an iodine content in the one or more ROIs. The processor is also programmed to determine a stenosis severity based on the measured iodine content and generate a report indicating the stenosis severity associated with the subject's vasculature. The system also includes an output for displaying the report.

In accordance with another aspect of the disclosure, a method for determining stenosis severity in a subject's vasculature using multi-energy computer tomography (MECT) imaging. The method includes acquiring multi-energy computed tomography (MECT) data using a CT system, performing a material decomposition process on acquired multi-energy CT data to generate one or more material density maps, and selecting, using the one or more material density maps, one or more regions of interest (ROIs) encompassing at least one vessel cross-section. The method also includes measuring an iodine content in the one or more ROIs, and determining a stenosis severity based on the measured iodine content. The method further includes generating a report indicating the stenosis severity associated with the subject's vasculature.

The foregoing and other advantages of the invention will appear from the following description.

DETAILED DESCRIPTION

Figure 1:
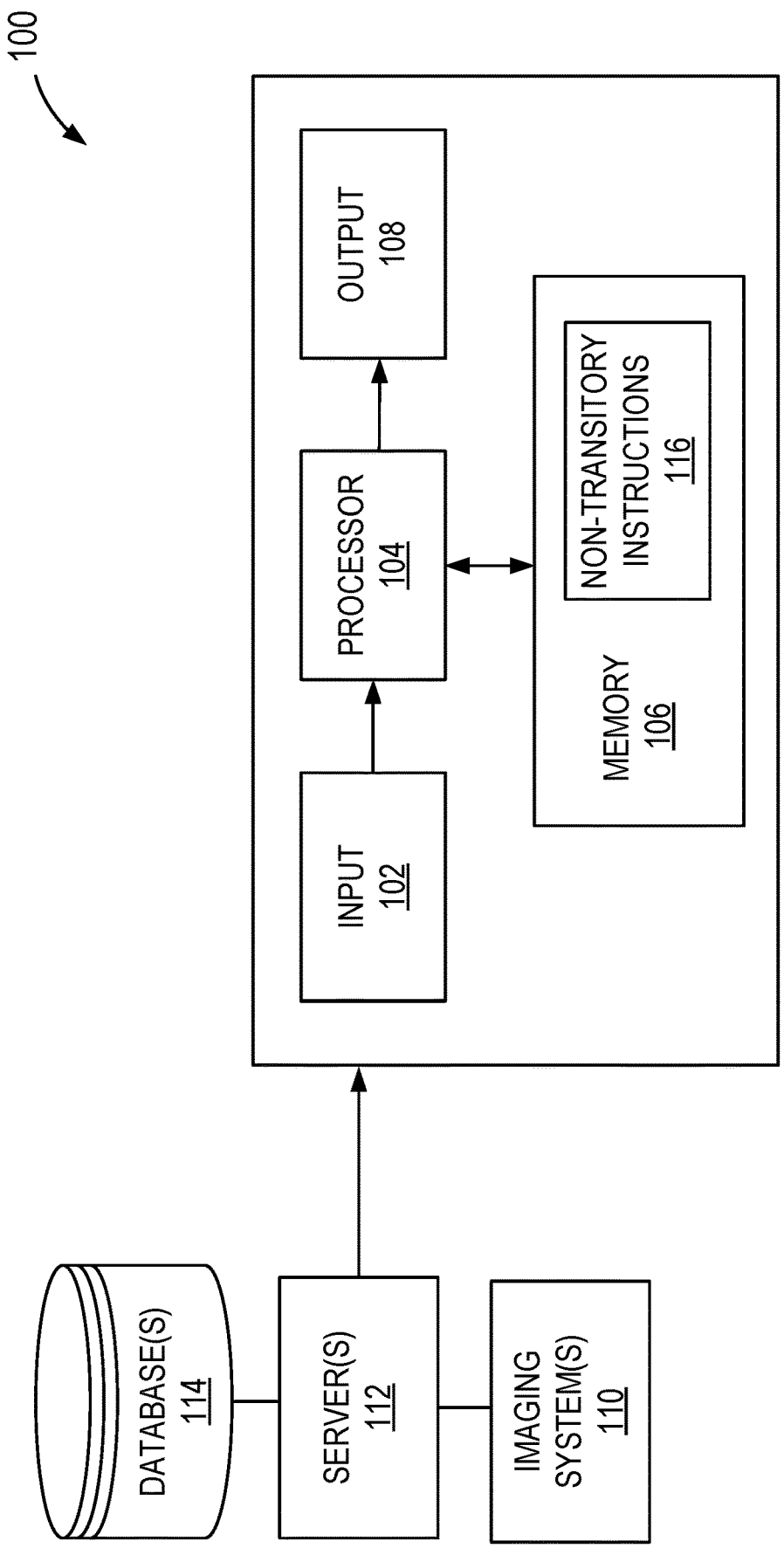
FIG. 1 shows a schematic diagram of a system, in accordance with aspects of the present disclosure.

Turning now to FIG. 1, a block diagram of an example system 100, in accordance with aspects of the present disclosure, is shown. In general, the system 100 can include an input 102, a processor 104, a memory 106, and an output 108, and may be configured to carry out steps, in accordance with methods described herein, including determining stenosis severity in a subject's vasculature using multi-energy computer tomography (MECT) imaging.

In general, the system 100 may be any device, apparatus or system configured for carrying out instructions for, and may operate as part of, or in collaboration with various computers, systems, devices, machines, mainframes, networks or servers. In some aspects, the system 100 may be a portable or mobile device, such as a cellular or smartphone, laptop, tablet, and the like. In this regard, the system 100 may be a system that is designed to integrate a variety of software and hardware capabilities and functionalities, and may be capable of operating autonomously.

Specifically, the input 102 may include different input elements, such as a mouse, keyboard, touchpad, touch screen, buttons, and the like, for receiving various selections and operational instructions from a user. The input 102 may also include various drives and receptacles, such as flash-drives, USB drives, CD/DVD drives, and other computer-readable medium receptacles, for receiving various data and information. In addition, as shown in FIG. 1, the system 100 may also communicate with one or more imaging systems 110, storage servers 112, or databases 114, by way of wired or wireless connection. To this end, input 102 may also include various communication ports and modules, such as Ethernet, Bluetooth, or WiFi, for exchanging data and information with these, and other external computers, systems, devices, machines, mainframes, servers or networks.

In addition to being configured to carry out various steps for operating the system 100, the processor 104 may also be programmed to determine stenosis severity in a subject's vasculature using MECT imaging. Specifically, the processor 104 may be configured to execute non-transitory instructions 116 stored in memory 106 to receive MECT data acquired using a CT system from the input 102 and process the data, in accordance with the present disclosure. Example MECT data may include spectral or dual-energy data, or any other realization of MECT data (e.g. separate single energy scans).

The processor 104 may then perform a material decomposition process on the received MECT data to generate various material density maps, each map indicative of a basis material. To do so, the processor 104 may apply various image-based or projection-based decomposition algorithms, or any combinations thereof. Example material density maps include iodine, water, calcium, and other materials.

Using the generated material density maps, the processor 104 may then be programmed to measure material content in selected regions of interest (ROIs), such as ROIs associated with or encompassing vessel cross-sections. To this end, in some aspects, the processor 104 may be programmed to select various ROIs by applying different automated or semi-automated segmentation algorithms. Alternatively, or additionally, user input may be used to select the ROIs. The selected ROIs may or may not include a luminal stenosis.

Iodine typically exists only inside the blood of the subject and is homogeneously distributed. As such, the processor 104 may be programmed to measure iodine content in an ROI by computing the sum of iodine concentration multiplied with the pixel volume of the ROI. The measured iodine content may then be used determine the stenosis severity. In particular, the processor 104 may calculate the ratio of iodine content between vasculature sites with and without luminal stenosis, according to the following:

$$\text{Stenosis Severity (\%)} = \left(1 - \frac{\sum I_{Stenosis}}{\sum I_{No\ Stenosis}}\right) \times 100; \quad (1)$$

where $\Sigma I$ is the integration of pixel intensities inside of a ROI(s) in the material density map.

The above calculations were derived as follows. Multi-energy CT measures the material-specific and energy dependent attenuation properties of materials with different elemental compositions and densities. From a material decomposition point of view, the CT measurement of a pixel with a spatial coordinate (x,y) at different energies E, $\overrightarrow{CT_E(x,y)}$, can be expressed as:

$$\overrightarrow{CT_E(x,y)} = M_{E\times N} \times \overrightarrow{\rho_N(x,y)} \quad (2).$$

Here, M is a material matrix of size E×N and it only depends on the basis material, the x-ray spectrum, and the detector response. Here we assume that M does not change with spatial coordinates (x,y). $\overrightarrow{\rho_N(x,y)}$ is an N×1 vector and represents the measured densities for N basis materials.

Here we assume that multi-energy CT systems can be treated as linear, shift-invariant (LSI) systems or at least locally LSI. Therefore, the multi-energy CT measurement, $\overrightarrow{CT_E(x,y)}$, can be expressed as:

$$\overrightarrow{CT_E(x,y)} = PSF(x,y) * \overrightarrow{CT_{E,T}(x,y)} = PSF(x,y) * (M_{E\times N} \times \overrightarrow{\rho_{N,T}(x,y)}) \quad (3).$$

Here, PSF(x,y) is the corresponding point spread function. $\overrightarrow{CT_{E,T}(x,y)}$ and $\overrightarrow{\rho_{N,T}(x,y)}$ represent the true signal T of multi-energy CT numbers and basis material densities.

By combining (2) and (3) gives:

$$M_{E\times N} \times \overrightarrow{\rho_N(x,y)} = \text{PSF}(x,y) * \overrightarrow{CT_{E,T}(x,y)} = \text{PSF}(x,y) * (M_{E\times N} \times \overrightarrow{\rho_{N,T}(x,y)}) \quad (4).$$

With accurate material decomposition, this gives:

$$\overrightarrow{\rho_N(x,y)} = \text{inv}(M_{E\times N}) \times \overrightarrow{CT_E(x,y)} = \text{PSF}(x,y) * \overrightarrow{\rho_{N,T}(x,y)} \quad (5).$$

In the iodine density map $\rho_I(x,y)$, we can measure the iodine content (or the total mass of iodine) inside a ROI, which is equal to the integration of the iodine density inside the ROI multiplied by the pixel volume V:

$$V \times \int_{X_{min}}^{X_{max}} \int_{Y_{min}}^{Y_{max}} \rho_I(x, y) dx dy = \quad (6)$$

$$V \times \int_{X_{min}}^{X_{max}} \int_{Y_{min}}^{Y_{max}} [\text{PSF}(x, y) * \rho_{I,T}(x, y)] dx dy =$$

$$V \times \int_{X_{min}}^{X_{max}} \int_{Y_{min}}^{Y_{max}} \text{PSF}(x, y) dx dy \times \int_{X_{min}}^{X_{max}} \int_{Y_{min}}^{Y_{max}} \rho_{I,T}(x, y) dx dy =$$

$$V \times k \times \int_{X_{min}}^{X_{max}} \int_{Y_{min}}^{Y_{max}} \rho_{I,T}(x, y) dx dy;$$

where k is the integration of point spread function inside the ROI and $\rho_{I,T}(x,y)$ represents the true iodine density. Here, for simplification, the ROI is defined as a rectangular with dimensions ($X_{min}$:$X_{max}$, $Y_{min}$:$Y_{max}$) but (6) can be generalized for any shape ROIs.

If we assume that iodine exists only inside the lumen and is uniformly distributed, the iodine content can be expressed as:

$$V \times \int_{X_{min}}^{X_{max}} \int_{Y_{min}}^{Y_{max}} \rho_I(x, y) dx dy = \quad (7)$$

$$V \times k \times \int_{X_{min}}^{X_{max}} \int_{Y_{min}}^{Y_{max}} \rho_{I,T}(x, y) dx dy = V k \tau \rho_{I,T};$$

where $\tau$ represents the total number of iodine-containing pixels inside the lumen (or iodine pixels) in the ROI.

From (7), we can demonstrate that the percent area luminal stenosis (or % Stenosis) can be obtained by using the ratio of the measured iodine content between vessel locations with and without a stenosis:

$$\% \text{ Stenosis} = \left(1 - \frac{\left[V \times \int_{X_{min}}^{X_{max}} \int_{Y_{min}}^{Y_{max}} \rho_I(x, y) dx dy\right]_{Stenosis}}{\left[V \times \int_{X_{min}}^{X_{max}} \int_{Y_{min}}^{Y_{max}} \rho_I(x, y) dx dy\right]_{Stenosis\ Free}}\right) \times 100\% = \quad (8)$$

$$\left(1 - \frac{[V k \tau \rho_{I,T}]_{Stenosis}}{[V k \tau \rho_{I,T}]_{Stenosis\ Free}}\right) \times 100\% =$$

$$\left(\frac{\tau_{Stenosis\ Free} - \tau_{Stenosis}}{\tau_{Stenosis\ Free}}\right) \times 100\%.$$

Hence, the proposed approach is equivalent to accurate segmentation of iodine pixels (or luminal area) for the measurement of percent area luminal stenosis.

Using the above, a percent of luminal area indicating a degree of stenosis may be determined by the processor 104. The processor 104 may be further configured to compute other quantitative metrics indicative of stenosis severity.

Figure 2:
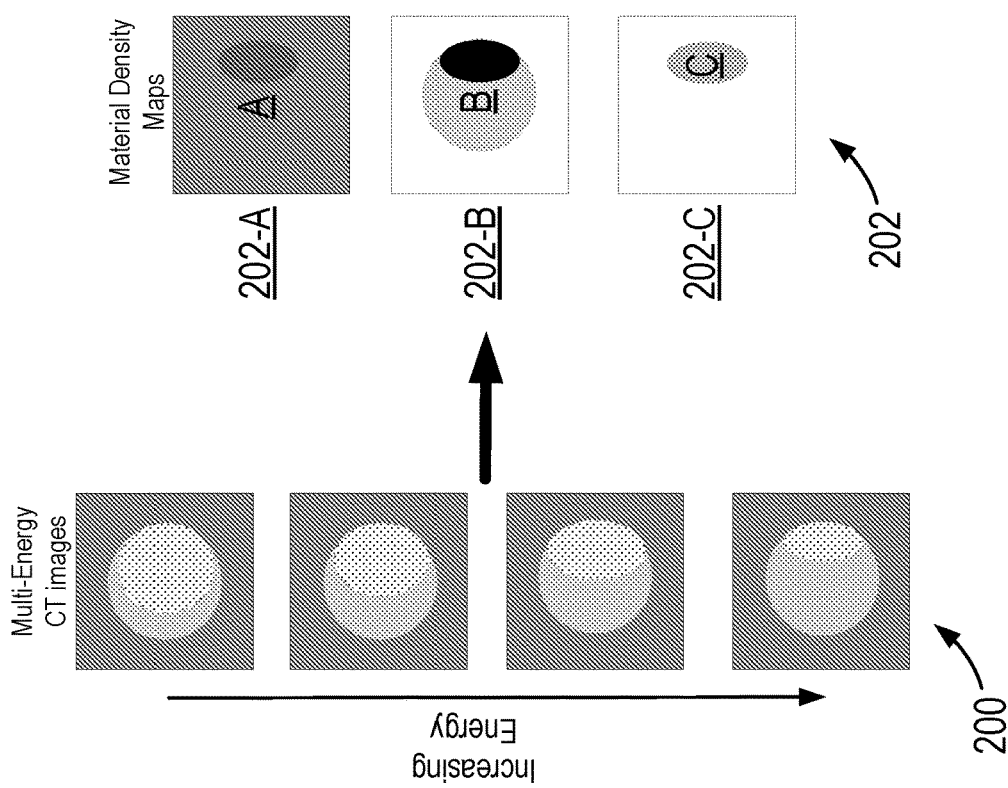
FIG. 2 is a schematic illustrating a method for quantifying stenosis severity, in accordance with aspects of the present disclosure.

By way of example, FIG. 2 illustrates this process in a schematic. In particular, FIG. 2 shows MECT images 200 with increasing energies of an example vessel cross-section. Due to different contrast produced by different x-ray energies, the same stenosis in the vessel can appear differently, and hence result in different measured stenosis severity. Therefore, at step 1, the MECT images 200 are used in a material decomposition process to generate 3 different material density maps 202. Each material density map 202-A, 202-B, and 202-C is indicative of a different material density, namely an A, B, and C, as shown. In this example, A, B and C represent water, iodine, calcium density, respectively. Using an ROI 206 that encompasses the vessel cross-section, the iodine content or mass may be determined using pixels intensities in density map 202-B. To determine the degree a stenosis, another iodine density map of a reference site (shown as 204-B in FIG. 2) may be generated in a similar manner using another set of MECT images. In clinical practice, such reference site is a vessel cross section without stenosis, which is selected from a location upstream or downstream on the same vessel, or from another branch vessel, such as the left and right carotid arteries. By taking the ratio of iodine content or mass computed from 202-B and 204-B, according to Eqn. 1, the percent of luminal area stenosis may be determined. Iodine mass is the product of iodine density and pixel volume. Since the pixel volume is typically constant in CT images, the ratio of summed iodine mass is also equal to the ratio between summed iodine densities.

Referring again to FIG. 1, the processor 104 may also be configured to generate a report, in any form, and provide it via output 108. In some aspects, the report may include information indicating the stenosis severity or degree of stenosis associated with the subject's vasculature. The report may also include raw or processed images, such as material density maps, as well as images indicating or highlighting various regions of a subject's vasculature, such as identified regions of stenosis, or regions associated with a particular material.

Figure 3:
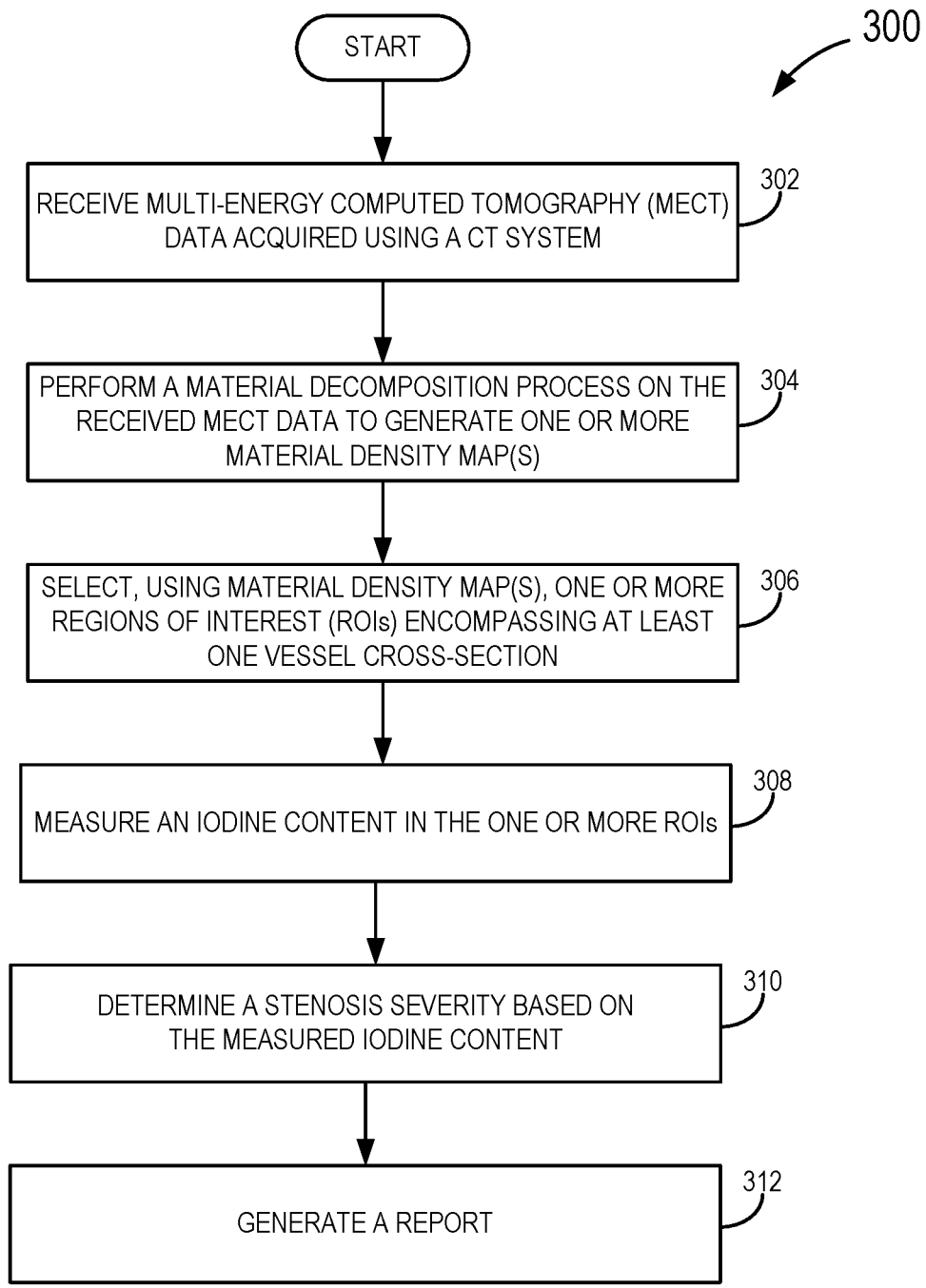
FIG. 3 is a flowchart setting forth steps of a process, in accordance with aspects of the present disclosure.

Turning now to FIG. 3, steps of a process 300 for determining stenosis severity in a subject's vasculature using MECT imaging are shown. The process 300 may be carried out using any suitable system, such as system 100 described with reference to FIG. 1.

The process 300 may begin at process block 302 with receiving MECT data acquired using a CT system. In particular, the MECT data may be accessed from a database, storage server or imaging system. In some aspects, steps may be carried out at process block 302 to acquire MECT data using a dual-energy CT system or a spectral CT system. The MECT data may be pre-processed as necessary. For example, the MECT data may be pre-processed to remove artifacts, or to generate one or more images in a reconstruction process.

Then, at process block 304, a material decomposition process may be performed on the received or acquired MECT data. In the material decomposition process, one or more material density maps may be generated, such as water density maps, iodine density maps, calcium density maps, and others. Using the generated density maps, one or more ROIs may then be selected. Alternatively, other images may be used to select the ROIs. As shown in FIG. 3, the ROIs may encompass a vessel cross-section. As described, the ROIs may be automatically selected by performing an automated or semi-automated segmentation algorithm. Alternatively, or additionally, the ROIs may be selected by a user. The selected ROIs may or may not include a luminal stenosis.

Then at process block 308, an iodine content may be measured in one or more selected ROIs. Based on the measured iodine content, a stenosis severity may be determined, as indicated by process block 310. As described, a ratio of iodine content between sites with and without luminal stenosis may be used to determine a percent of luminal area indicating a degree of stenosis. A report may then be generated at process block 312, as described above.

Figure 4:
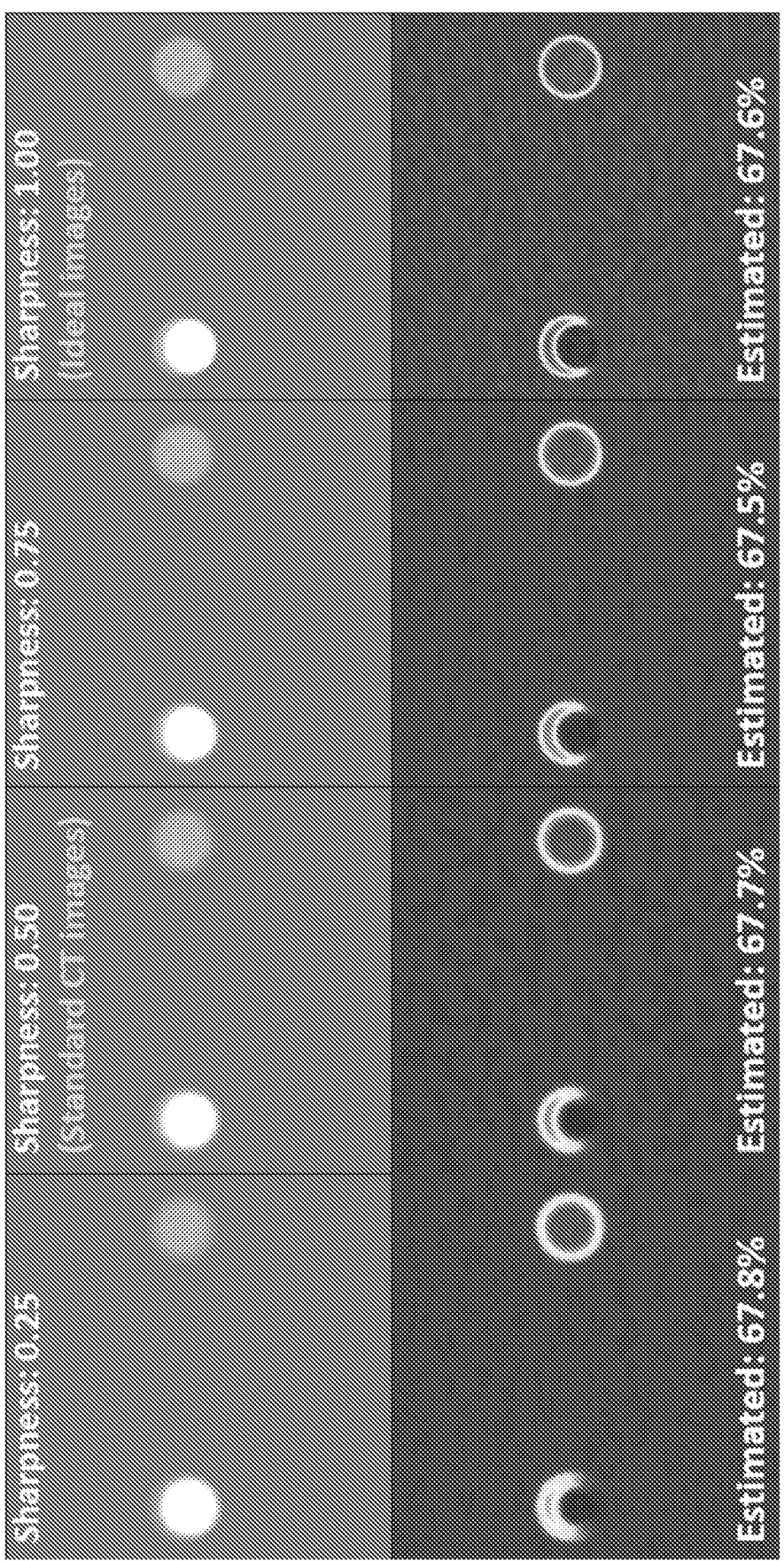
FIG. 4 are images demonstrating accurate stenosis severity determination using images with different sharpness, using the method of the present disclosure.
Figure 10B:
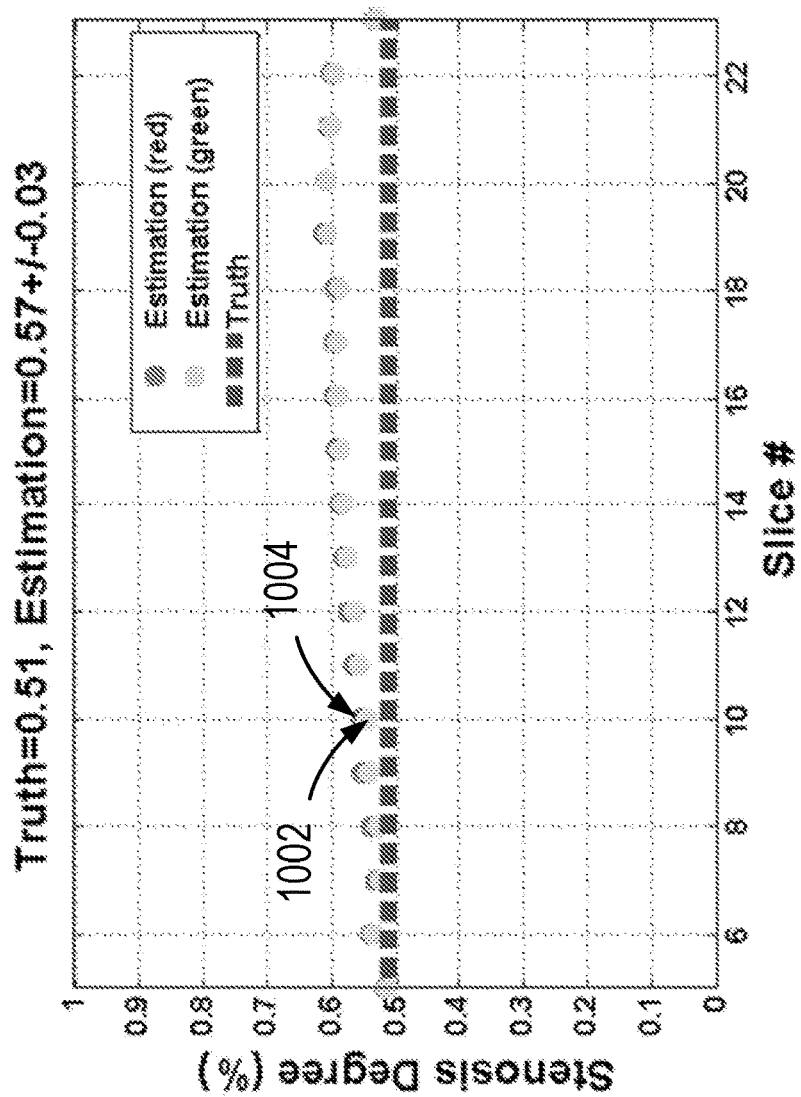
FIG. 10B is a graph showing the degree of stenosis determined in accordance with present disclosure using the two ROIs depicted in FIG. 10A.
Figure 10A:
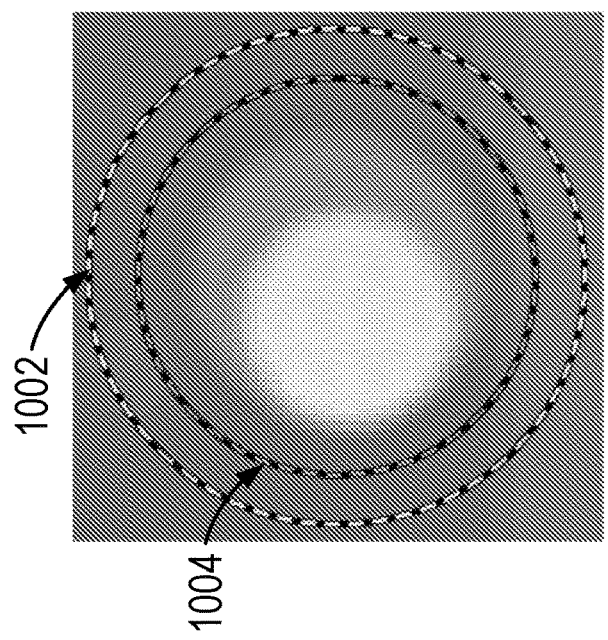
FIG. 10A is an example image of a simulated phantom measured using two different regions of interest (ROIs) selected.

To validate the present approach, a computer simulation was performed. In particular, a digital phantom was generated simulating blood vessel cross-sections with a diameter of approximately 7.6 mm. Blood vessels with 67% stenosis and without stenosis were simulated. Spectral CT images with four different sharpness values (or spatial resolution) were generated by performing CT simulation and reconstruction. The results are shown in FIG. 4, for CT images varying having sharpness 0.25, 0.50 (standard CT images), 0.75 and 1.00 (ideal images). Using the method described herein stenosis severity was estimated to be 67.8%, 67.7%, 67.5% and 67.6%, respectively. These results demonstrate very accurate estimation of the degree of stenosis, regardless of image sharpness.

thermore, as illustrated in FIGS. 10A and 10B, the present approach is free from laborious threshold adjustments and labor-intensive segmentation. In particular, FIG. 10A shows an example CT image with different selected ROIs, namely 1002 and 1004, encompassing a simulated vessel cross-section. As shown in FIG. 10B, a high agreement in the determined degree of stenosis is achieved between the different ROIs. This illustrates that the present approach can achieve high reproducibility with reduced inter and intra user variability.

Further studies were also performed. For example, further computer simulations were used to verify the work. A digital phantom was used to simulate a cross section of a blood vessel with ~66.6% area stenosis and a reference blood vessel without a stenosis. The vessels were filled with 13.6 mg/ml iodine solution, which yielded contrast levels relevant to clinical contrast-enhanced CT exams (around 350 HU at 120 kV). A cylinder containing 406.5 mg/ml calcium chloride was placed in the vessel to mimic a high density calcification (around 1300 HU at 120 kV) and create a severe stenosis.

A CT simulation software package (DRASIM, Siemens Healthcare) was used to generate projection data at four monoenergetic energies, 30, 50, 70, and 90 keV. To assess the impact of the point spread function on the estimation accuracy, images with four different sharpness levels (i.e.

TABLE 1

Image acquisition parameters.

| Scan | | 5C | DECT (Carotid-CTA) |
|---|---|---|---|
| kV | 140 | 120 | 100/Sn140; 80/Sn140 |
| Detector mode | PCD | EID | EID |
| Scan mode | Helical | Helical | Helical |
| Collimation | 32 × 0.5 mm | 32 × 0.6 mm | 32 × 0.6 mm |
| Effective mAs | 68/550 mAs | 56/499 mAs | 50/408/mAs |
| Rotation time | 1.0 s | 0.5 s | 0.5 |
| Pitch | 0.6 | 0.7 | 0.6 |
| Thresholds (keV) | [21, 31, 55, 90] | n/a | n/a |
| | [20, 25, 57, 77] | | |
| | [20, 39, 64, 89] | | |
| | [25, 45, 65, 85] | | |
| | [25, 65] | | |
| Slice thickness | | 1.5/1.0 mm | |
| Recon kernel | | D30 | |
| CTDIvol (32 cm)* | 8.68/60.74 mGy | 3.82/33.35 mGy | 3.53/28.13 mGy |

Figure 5:
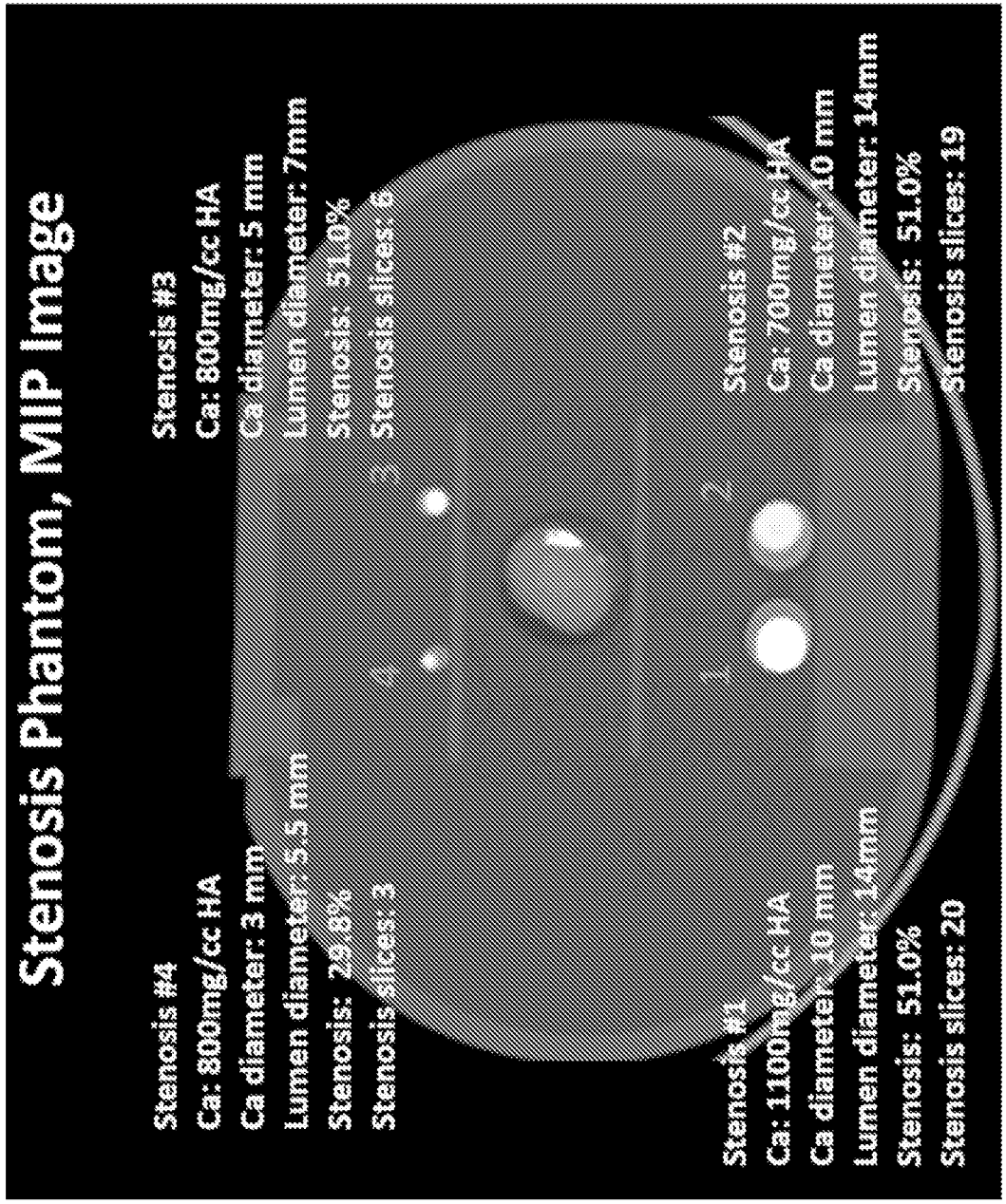
FIG. 5 is a CT image showing phantoms that simulate different stenosis size and severity.

In addition, physical phantom experiments were performed to evaluate the present approach. Specifically, stenosis phantoms were fabricated using various tubes and high density calcium cylinders with known dimensions. Four stenosis regions with various degrees of stenosis, size, and calcification were simulated (FIG. 5). Iodine contrast inside the lumens was matched to values used in clinical exams. The phantoms were imaged using data acquisition parameters as detailed in Table 1.

Figure 6:
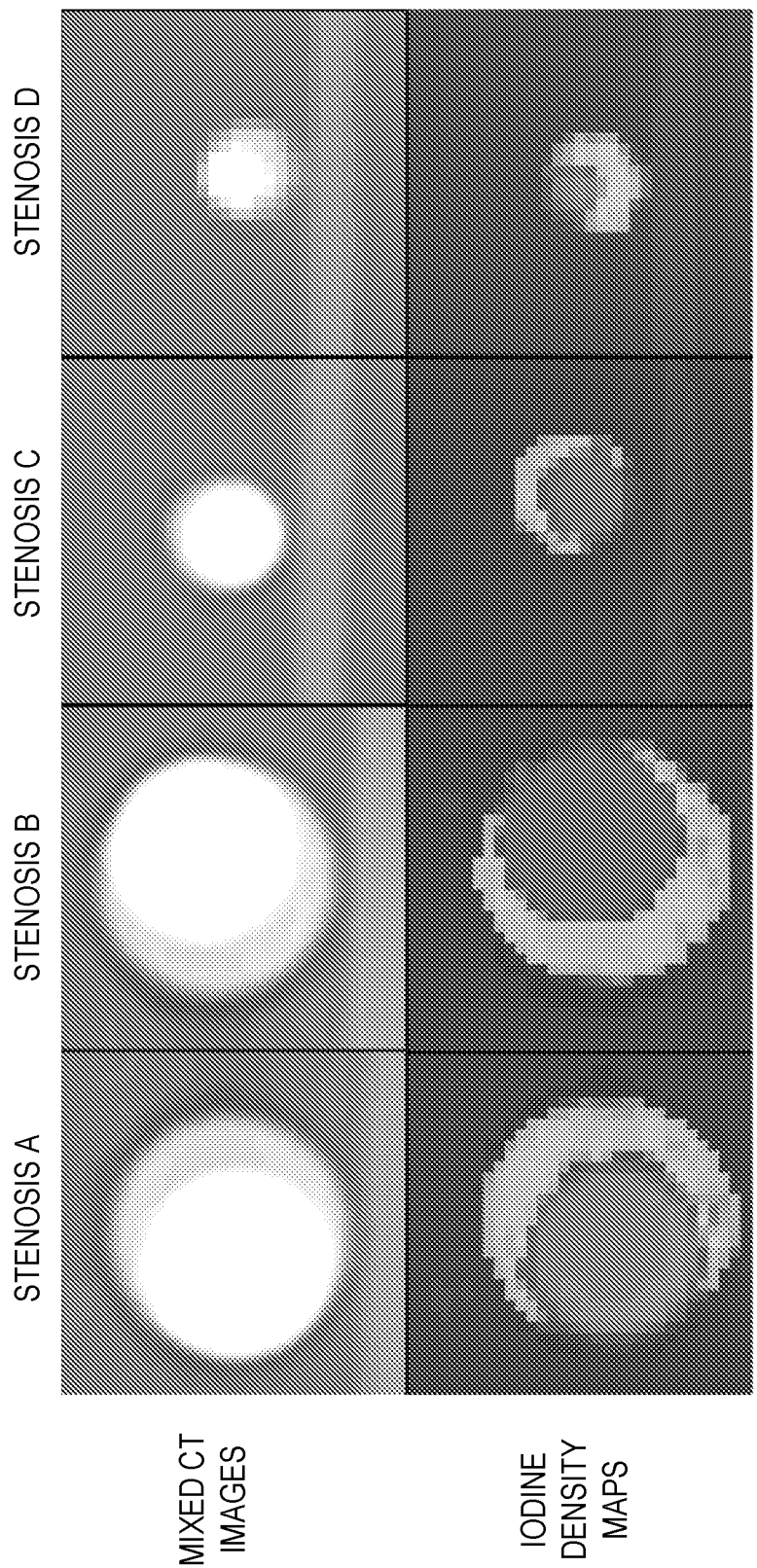
FIG. 6 are example images and iodine density maps of the simulated phantoms of FIG. 5.
Figure 7:
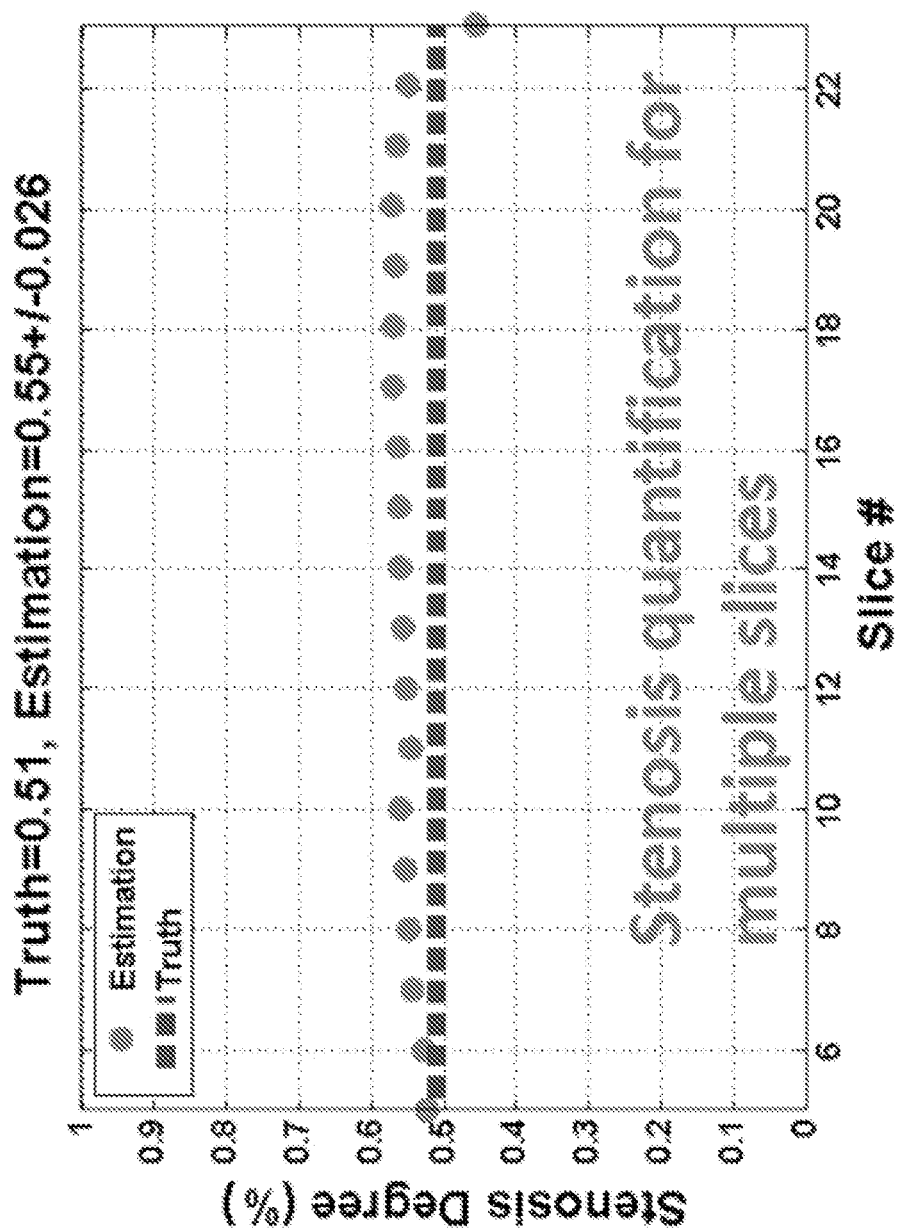
FIG. 7 is a graph showing stenosis measurements of a phantom, determined in accordance with the present disclosure, compared to the ground truth.
Figure 8:
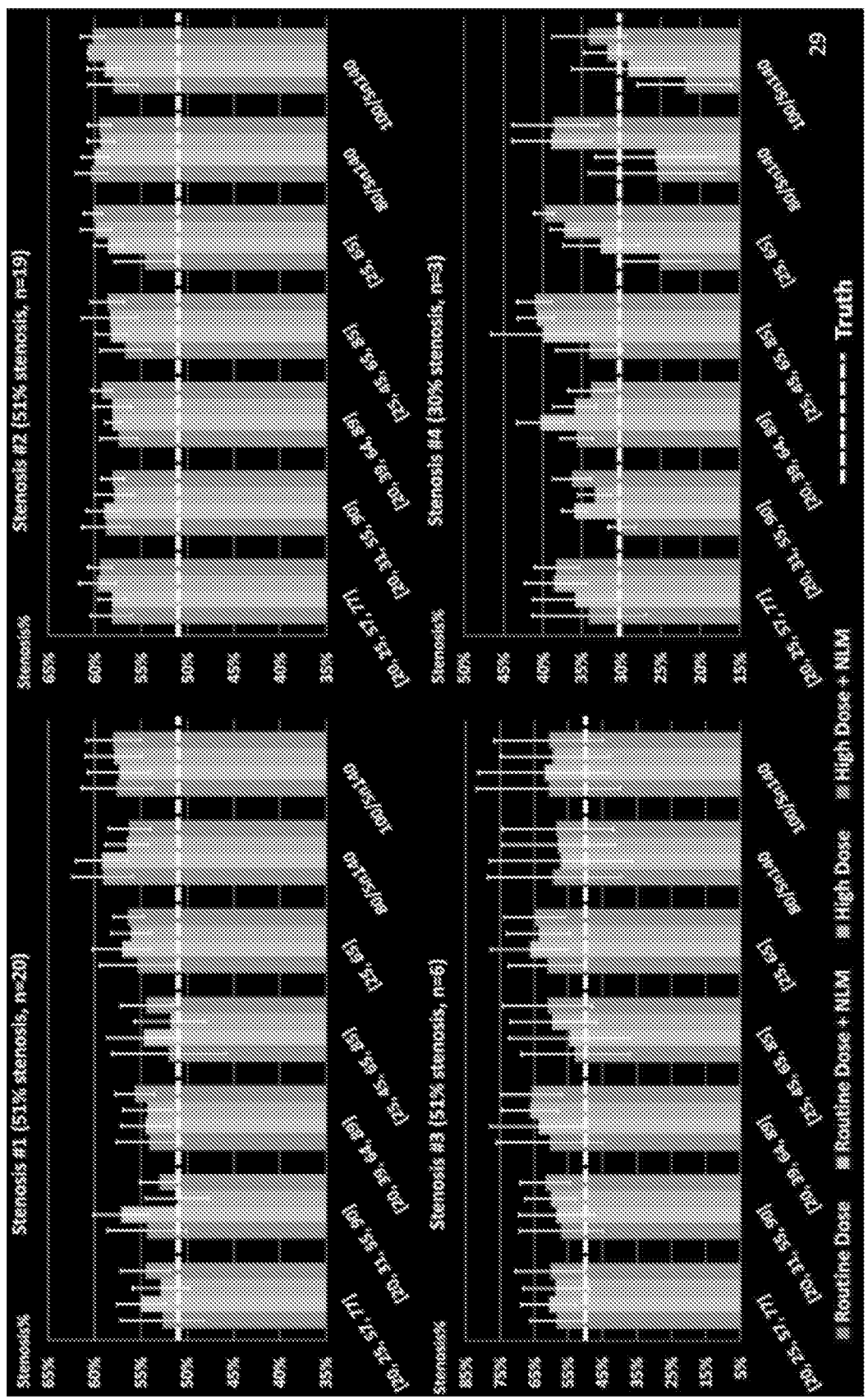
FIG. 8 is a graph showing the estimation accuracy of the present approach for the simulated phantoms of FIG. 5.
Figure 9:
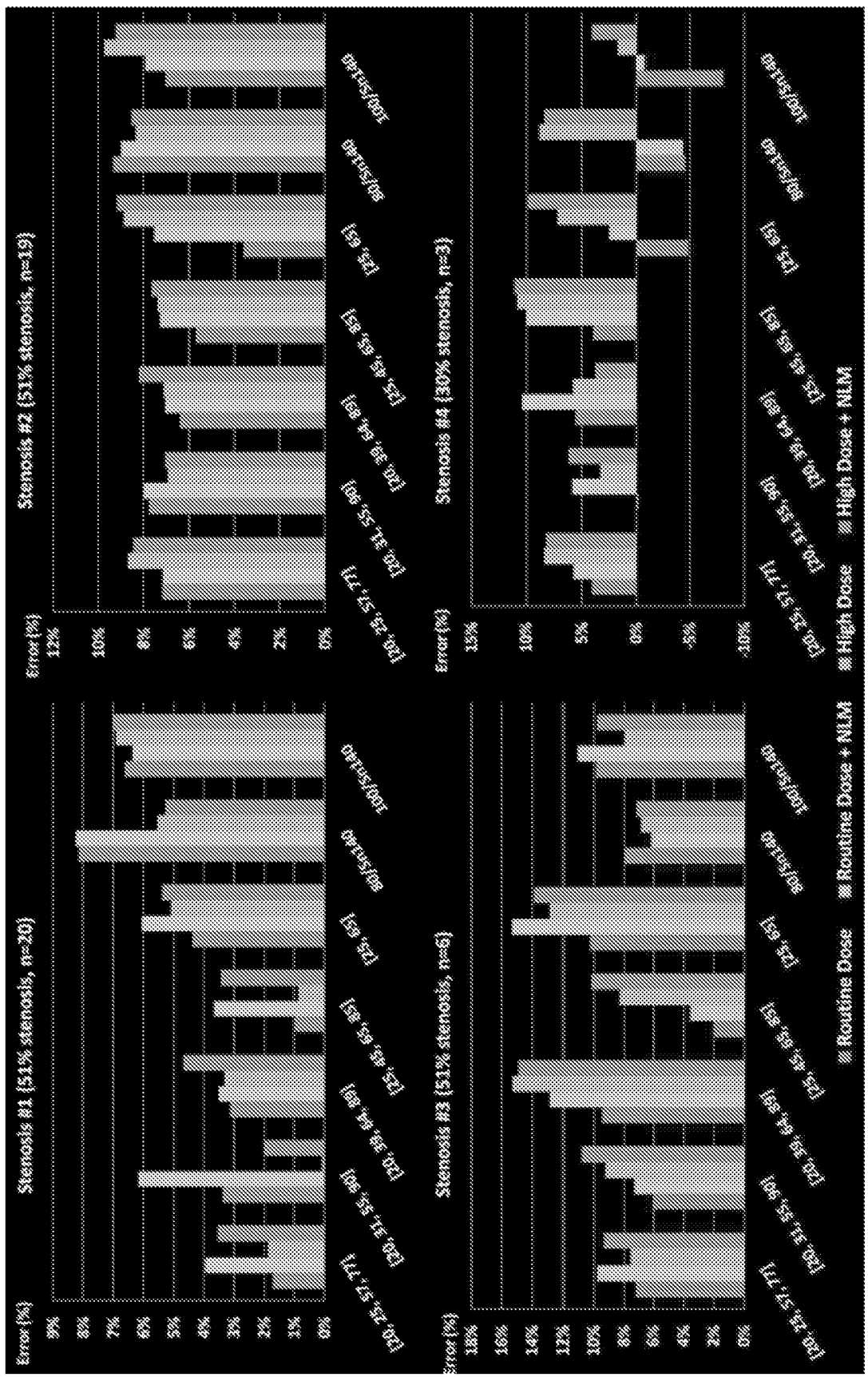
FIG. 9 is a graph showing the estimation error of the present approach for the simulated phantoms of FIG. 5.

As described, iodine density maps were generated from the acquired CT images (FIG. 6). Using generated iodine maps, a degree of stenosis for various CT slices was estimated and compared to the ground truth, as illustrated in the example of FIG. 7, illustrating quite accurate quantification of stenosis severity. The robustness of the present approach for determining stenosis severity was tested for different imaging conditions. The results are summarized FIG. 8 and FIG. 9, showing estimation accuracy and estimation error, respectively. In particular, no strong dependence on image acquisition parameters was observed. Furspatial resolution) were reconstructed using a filtered-back-projection (FBP) algorithm with different reconstruction kernels.

Material decomposition was performed on the four monochromatic, multi-energy CT images using an in-house image-based material decomposition method. Two circular ROIs of the same size were drawn in the iodine density maps to measure the iodine content. Finally, the percent area luminal stenosis was determined by the ratio between the two iodine content values.

In this study, we focused on the evaluation of stenosis severity of carotid arteries. We performed a series of phantom experiments to test the proposed method. Four phantoms with different degrees of stenosis (30 to 51%), vessel diameters, and calcification densities were fabricated using hydroxyapatite (HA) cylinders and test tubes filled with iodinated solutions (FIG. 3). We purposely chose four high-density HA cylinders (At 120 kV, the CT numbers were 1478 HU, 1108 HU, 1108 HU, and 972 HU, respectively) to demonstrate that the proposed method could achieve accurate estimation of stenosis severity even for very dense calcifications, a practical problem for all conventional CTA-based methods. The tubes were filled with 30 mg/ml Iohexol solution (Iohexol, 350 mgI/ml [Omnipaque; GE Healthcare, Shanghai, China]) with contrast levels relevant to clinical contrast-enhanced CT exams (e.g. about 350 HU contrast enhancement at 120 kV). The dimensions of the HA cylinders and test tubes were measured by a caliber.

The same analysis was performed on all four sets of multi-energy CT images with different sharpness levels and the accuracy of stenosis measurements was assessed.

Conventional SECT images were acquired using a commercial dual-source CT (DSCT) system (Somatom Flash, Siemens Healthcare) operating in single source mode and the routine carotid CTA single-energy protocol used in our clinical practice. Multi-energy CT images were also acquired from a research PCCT scanner (Somatom CounT, Siemens) using a mode that simultaneously generates 4 measurements at 4 different X-ray energy thresholds using a single exposure. Additionally, images were also acquired using the commercial DSCT scanner (operating in dual-energy mode) and from the PCCT scanner using a mode that simultaneously generates 2 measurements at 2 different X-ray energy thresholds using a single exposure. The data acquisition and image reconstruction parameters are listed in Table 2.

measurements. An additional volume conservation assumption was required for DECT and PCCT macro images to decompose three basis materials from measurements at only two energies. The stenosis measurements were performed at multiple slices along the long axis of the calcium cylinder and the estimation error was calculated.

For the SECT images, stenosis severity was analyzed with a commercial stenosis analysis software package (Syngo Via CT vascular, Siemens). After loading CTA images, multi-planar reformations (MPR) images and volume rendering techniques (VRT) images were created and displayed to the operator. The evaluation of vessel lumen was performed using the curved planar reformations (CPR) view. Digital calipers were used to quantify stenosis severity using default parameter settings (lower threshold: 50 HU; upper threshold: 940 HU). One caliper was used to mark the stenosis and two reference pointers were used as reference markers proximal and distal to the stenosis. Percentage area luminal stenosis was then calculated.

Computer simulation results showed that multi-energy CT images with different degree of sharpness caused large variations in the appearance of the same stenosis. However, the method of the present disclosure estimated the percent area luminal stenosis with errors below 1.2%. The estimation accuracy was almost identical for the four different

TABLE 2

Acquisition and reconstruction parameters used in the phantom experiments.

| Scan Parameters | SECT | PCCT 4-threshold mode | PCCT 2-threshold mode | DECT | |
|---|---|---|---|---|---|
| kV | 120 | 140 | 140 | 80/Sn140 | 100/Sn140 |
| Detector Type | EID | PCD | PCD | EID | |
| Collimation (mm) | 128 × 0.6 | 32 × 0.5 | 32 × 0.5 | 32 × 0.6 | |
| Pitch | 0.7 | 0.6 | 0.6 | 0.6 | |
| Thresholds (keV) | N/A | [20, 31, 55, 90] [20, 25, 57, 77] [20, 39, 64, 89] [25, 45, 65, 85] | [25, 65] | N/A | |
| Slice Thickness/Interval | 1.5/1.0 mm | 1.5/1.0 mm | 1.5/1.0 mm | 1.5/1.0 mm | |
| Recon Kernel | B40 | D30 | D30 | D30 | |
| Recon Fov (mm) | 200 | 200 | 200 | 200 | |
| CTDIvol (32 cm) (mGy) | Rd: 3.82 | Rd: 8.68 Hd: 60.74 | Rd: 3.88 Hd: 60.74 | Rd: 3.52 Hd: 18.50 | Rd: 3.53 Hd: 28.13 |

The radiation dose levels for DECT and PCCT macro acquisitions matched the routine dose (RD) level used in the SECT exam (Table 2). For the PCCT 4-threshold acquisition, the radiation dose was doubled because this mode has only 50% detector dose efficiency. This delivered the same photon fluence to the detector as the other acquisitions in order to make a fair comparison. A commercial PCCT would not use this special research mode and hence would not require this dose doubling. We performed two tests to assess the impact of image noise on the estimation accuracy. First, an in-house image-domain noise reduction method, multi-energy non-local means (MENLM), was applied to the RD images to achieve around 80 to 90% noise reduction. Secondly, additional scans with the highest dose (HD) levels achievable were performed for the DSCT (dual-energy mode) and PCCT systems.

A method in accordance with the present disclosure was applied for all three sets of dual- and multi-energy CT data: RD, MENLM filtered RD, and HD images. Three-basis material (calcium, iodine, and water) decomposition was performed to generate the iodine density maps for stenosis levels of sharpness, which demonstrated that the point spread function had no impact on the stenosis measurements.

Figure 11:
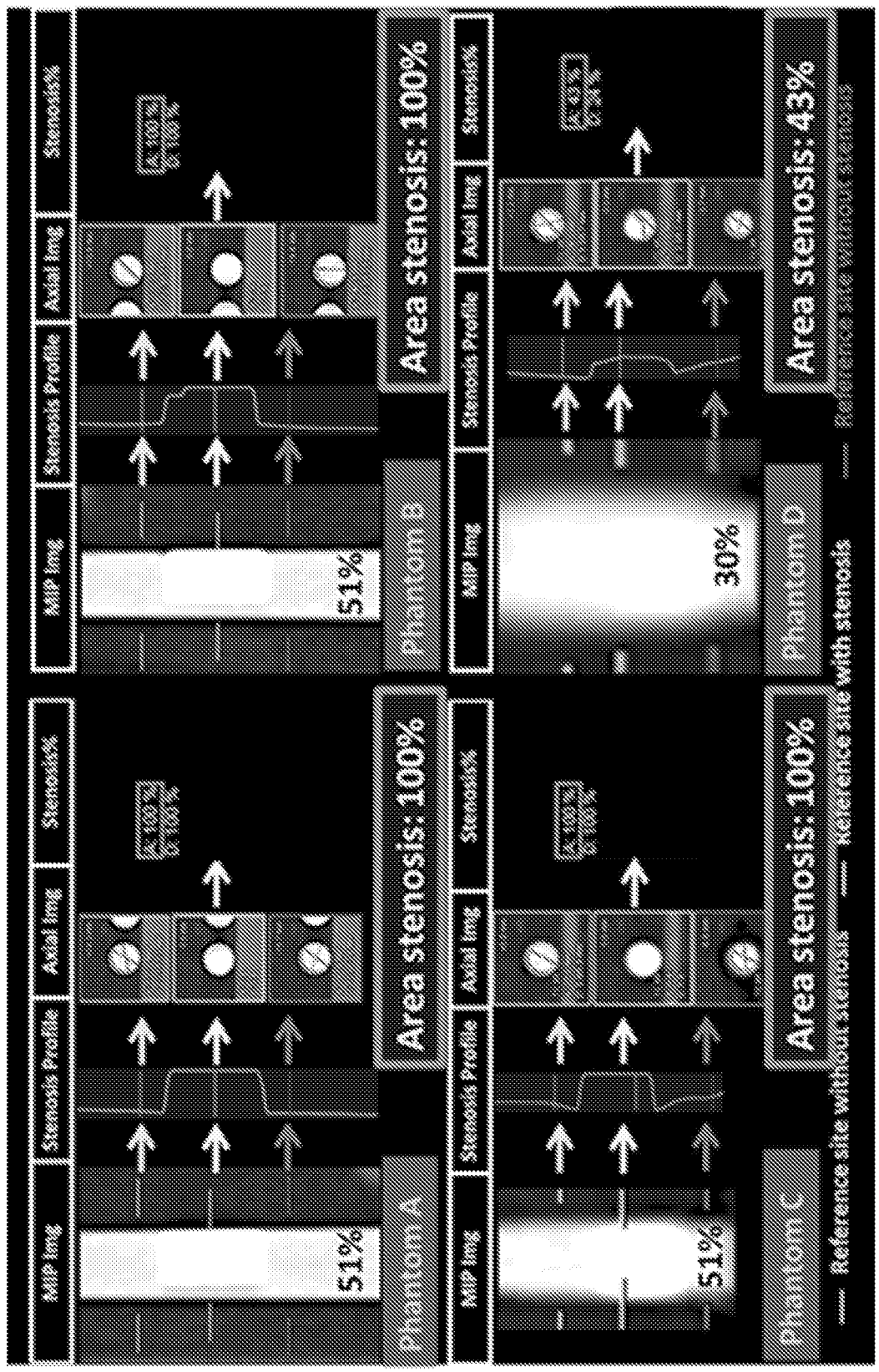
FIG. 11 is a set of images showing stenosis quantification results from the commercial stenosis quantification software using conventional CTA images.

With the presence of heavy calcifications, errors in the stenosis measurements using single-energy CT and the commercial software were very large, as illustrated in FIG. 11, ranging from 4.4% to 46%, and were especially worse in the presence of heavier and larger calcifications, resulting in serious misinterpretation of phantoms A-C as completely blocked vessels.

That is, FIG. 11 shows stenosis quantification results from the commercial stenosis quantification software using conventional CTA images. The intermediate lines on the gray-scale MIP images marks the reference site with stenosis, whereas the top and bottom lines were used as markers for the reference sites without stenoses. The stenosis analysis software reported the percentage of area stenosis of multiple sites in the form of a 1D profile, as well as the percent area stenosis at the reference site with stenosis (as marked by the red rectangular boxes). The axial images for the three reference sites were displayed together with automatic segmented luminal area. High density calcifications caused over-estimation of percent area luminal stenosis from conventional CTA exam: The estimated percent area stenoses were 100%, 100%, 100%, and 43% for phantoms A-D. (Actual percent luminal area stenosis was 51, 51, 51 and 30%, respectively).

In contrast, the material decomposition method in accordance with the present disclosure achieved good separation between iodine, calcium, and water, as illustrated in FIG. 6, thereby facilitating the use of iodine density maps for the quantification of percent area luminal stenosis. That is, FIG. 6 shows that material decomposition of multiple-energy CT images yielded good separation between iodine and calcium, thereby facilitating the quantification of stenosis severity. Top row: CT images of the four stenosis phantom after MENLM Filtering; Bottom row: Color-coded iodine density maps in the unit of mg/ml from the material decomposition. Also, color-coded calcium density maps can be generated.

For both DECT and PCCT systems, the systems and methods in accordance with the present disclosure provide accurate measurements of the percent area luminal stenosis from CT images using clinically relevant dose levels. For the stenosis phantoms containing very dense calcifications, the estimation errors were below, for example, 9% and 18% for MECT and DECT (including PCCT macro mode) images, respectively, which were much lower than that achieved from conventional single-energy CTA exams and segmentation-based measurements. Therefore, the present techniques can address the clinical limitations of single-energy CTA for stenosis severity quantification. This approach does not require laborious segmentation or careful adjustment of thresholds and therefore is both practical and efficient. Finally, because the present method measures stenosis severity based on the integration of iodine densities over ROIs, the influence of noise is mitigated by the integration. Hence, reducing image noise or increasing radiation dose did not affect the estimation accuracy. This shows that similar estimation accuracy can be achieved from low-radiation-dose screening exams, although this remains to be demonstrated in future work.

The systems and methods provided herein can achieve accurate and reproducible estimation of stenosis severity using multi-energy CT and can be readily deployed to commercial DECT systems available in clinical practice. Commercial software packages (e.g. material decomposition, centerline tracing) can be provided with only slight adaptation to work with this described approach for stenosis severity measurements.

Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A system for determining stenosis severity in a subject's vasculature using multi-energy computer tomography (MECT) imaging, the system comprising:
   an input configured to receive MECT data acquired using a CT system;
   a processor programmed to:
      perform a material decomposition process on received MECT data to generate one or more material density maps of the subject;
      select, using the one or more material density maps of the subject, a first region of interest (ROI) encompassing at least one vessel cross-section at a site with stenosis and a second ROI encompassing a vessel cross-section at a site without stenosis;
      measure an iodine content in the first ROI of the one or more material density maps of the subject and the second ROI of the one or more material density maps of the subject;
      calculate a ratio of iodine content between the first ROI and the second ROI;
      determine a stenosis severity based on the calculated ratio of iodine content;
      generate a report indicating the stenosis severity associated with the subject's vasculature; and
   an output for displaying the report.

2. The system of claim 1, wherein the MECT data comprises at least one of spectral computed tomography (SCT) image data and dual-energy computed tomography (DECT) image data.

3. The system of claim 1, wherein the processor is further programmed to generate at least one of calcium map, iodine map, and water map using received multi-energy CT data.

4. The system of claim 1, wherein the processor is further programmed to apply in the material decomposition process an image-based decomposition algorithm, a projection-based decomposition algorithm, or a combination thereof.

5. The system of claim 1, wherein the processor is further programmed to measure the iodine content by computing a sum of iodine concentration multiplied with a pixel volume.

6. The system of claim 1, wherein the processor is further programmed to determine the stenosis severity by quantifying a percent of luminal area covered by stenosis in the first ROI.

7. A method for determining stenosis severity in a subject's vasculature using multi-energy computer tomography (MECT) imaging, the method comprising:
   acquiring MECT data using a CT system;
   performing a material decomposition process on acquired MECT image data to generate one or more material density maps of the subject;
   selecting, using the one or more material density maps of the subject, a first region of interest (ROI) encompassing at least one vessel cross-section at a site with stenosis and a second ROI encompassing a vessel cross-section at a site without stenosis;
   measuring an iodine content in the first ROI of the one or more material density maps of the subject and the second ROI of the one or more material density maps of the subject;
   calculating a ratio of iodine between the first ROI and the second ROI;
   determining a stenosis severity based on the calculated ratio of iodine content; and
   generating a report indicating the stenosis severity associated with the subject's vasculature.

8. The method of claim 7, wherein the MECT image data comprises at least one of spectral computed tomography (SCT) image data and dual-energy computed tomography (DECT) image data.

9. The method of claim 7, wherein the method further comprises generating at least one of calcium map, iodine map, and water map using received multi-energy CT image data.

10. The method of claim 7, wherein the method further comprises applying in the material decomposition process an image-based decomposition algorithm, a projection-based decomposition algorithm, or a combination thereof.

11. The method of claim 7, wherein the method further comprises measuring the iodine content by computing a sum of iodine concentration multiplied with a pixel volume.

12. The method of claim 7, wherein the method further comprises determining a stenosis severity by quantifying a percent of luminal area covered by stenosis in the first ROI.

* * * * *